United States Patent
Kassab

(10) Patent No.: US 10,034,623 B2
(45) Date of Patent: Jul. 31, 2018

(54) DEVICES, SYSTEMS, AND METHODS FOR DETERMINING VEIN GEOMETRIC AND COMPLIANCE PROFILES FOR VENOUS STENTING

(71) Applicant: 3DT Holdings, LLC, San Diego, CA (US)

(72) Inventor: Ghassan S. Kassab, La Jolla, CA (US)

(73) Assignee: 3DT Holdings, LLC, San Diego, CA (US)

( * ) Notice: Subject to any disclaimer, the term of this patent is extended or adjusted under 35 U.S.C. 154(b) by 450 days.

(21) Appl. No.: 14/688,624

(22) Filed: Apr. 16, 2015

(65) Prior Publication Data

US 2015/0297110 A1 Oct. 22, 2015

Related U.S. Application Data

(60) Provisional application No. 61/980,364, filed on Apr. 16, 2014.

(51) Int. Cl.
*A61B 5/107* (2006.01)
*A61B 5/053* (2006.01)
(Continued)

(52) U.S. Cl.
CPC ........ *A61B 5/1076* (2013.01); *A61B 5/02007* (2013.01); *A61B 5/0538* (2013.01);
(Continued)

(58) Field of Classification Search
CPC ......... A61B 5/05; A61B 5/0538; A61B 5/103; A61B 5/107; A61B 5/1071; A61B 5/1072;
(Continued)

(56) References Cited

U.S. PATENT DOCUMENTS 7,454,244 B2 11/2008 Kassab et al.
7,479,120 B2 1/2009 Gregersen
(Continued)

OTHER PUBLICATIONS

McMahon, Barry P. et al., "The functional lumen imaging probe (FLIP) for the evaluation of the esophagogastric junction," Am J Physiol Gastrointest Liver Physiol, Aug. 31, 2006, pp. G377-G385, vol. 292, American Physiological Society, Beshesda, MD.

*Primary Examiner* — Adam J Eiseman
(74) *Attorney, Agent, or Firm* — Reichel Stohry LLP; Mark C. Reichel; Natalie J. Dean

(57) ABSTRACT

Devices, systems, and methods for determining vein geometric and compliance profiles for venous stenting. In one device embodiment, the device comprises an elongated body configured to fit within a mammalian luminal organ, a balloon coupled to the elongated body capable of and configured for inflation and deflation within the mammalian luminal organ, at least two excitation electrodes positioned along the elongated body within the balloon, and a plurality of at least three detection electrodes positioned in between at least two of the at least two excitation electrodes, wherein a first pair of two adjacent detection electrodes of the at least three detection electrodes can detect an electric field generated by the at least two excitation electrodes and obtain a first conductance measurement within the balloon, and a second pair of two adjacent detection electrodes can detect the electric field and obtain a second conductance measurement within the balloon.

20 Claims, 8 Drawing Sheets

(51) Int. Cl.
  *A61B 5/00* (2006.01)
  *A61B 5/02* (2006.01)
  *A61F 2/82* (2013.01)

(52) U.S. Cl.
  CPC .......... *A61B 5/1077* (2013.01); *A61B 5/6853* (2013.01); *A61F 2/82* (2013.01)

(58) Field of Classification Search
  CPC ....... A61B 5/1073; A61B 5/1076; A61B 5/68; A61B 5/6852; A61B 5/6853; A61B 5/053; A61B 5/02007; A61B 2017/0026
  See application file for complete search history.

(56) References Cited

U.S. PATENT DOCUMENTS

| | | |
|---|---|---|
| 8,078,274 B2 | 12/2011 | Kassab |
| 8,099,161 B2 | 1/2012 | Kassab |
| 8,114,143 B2 | 2/2012 | Kassab et al. |
| 8,406,867 B2 | 3/2013 | Kassab |
| 8,465,452 B2 | 6/2013 | Kassab |
| 8,632,469 B2 | 1/2014 | Kassab |
| 8,886,301 B2 | 11/2014 | Kassab |
| 2009/0182287 A1 | 7/2009 | Kassab |
| 2017/0196478 A1* | 7/2017 | Hunter .................. A61B 5/065 |

* cited by examiner

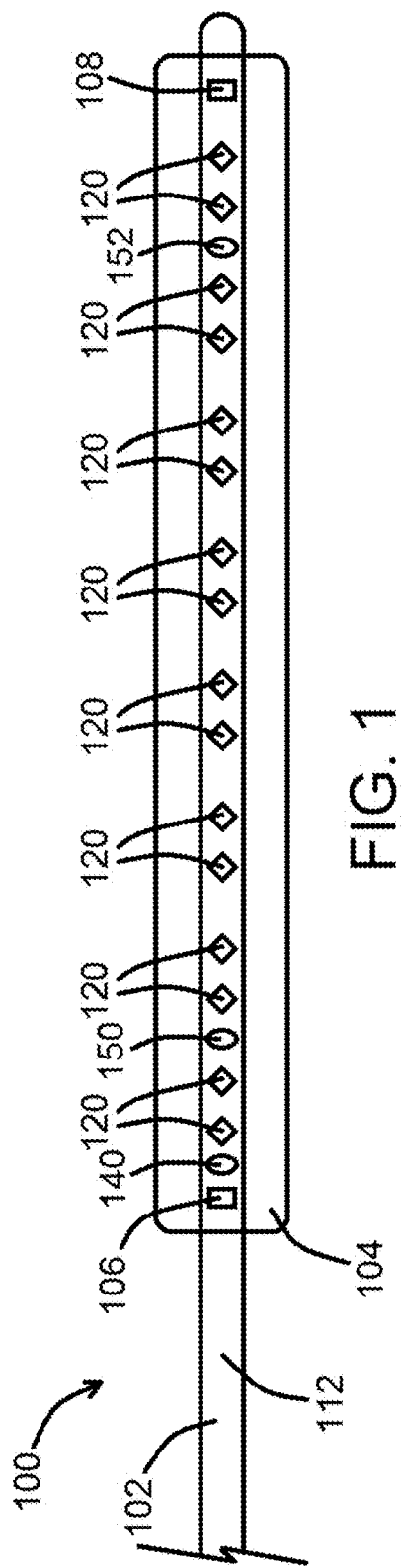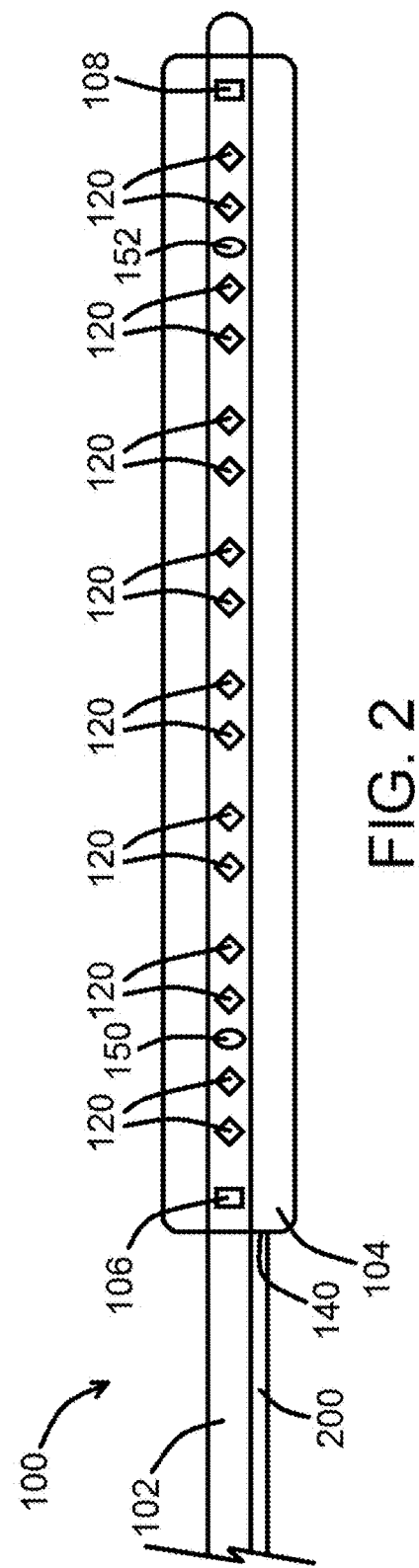

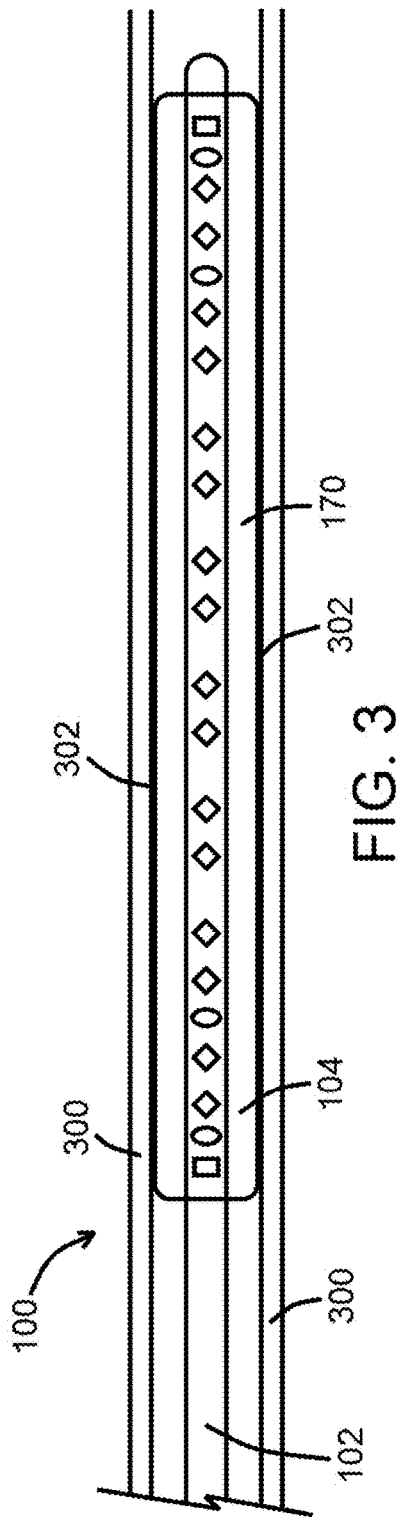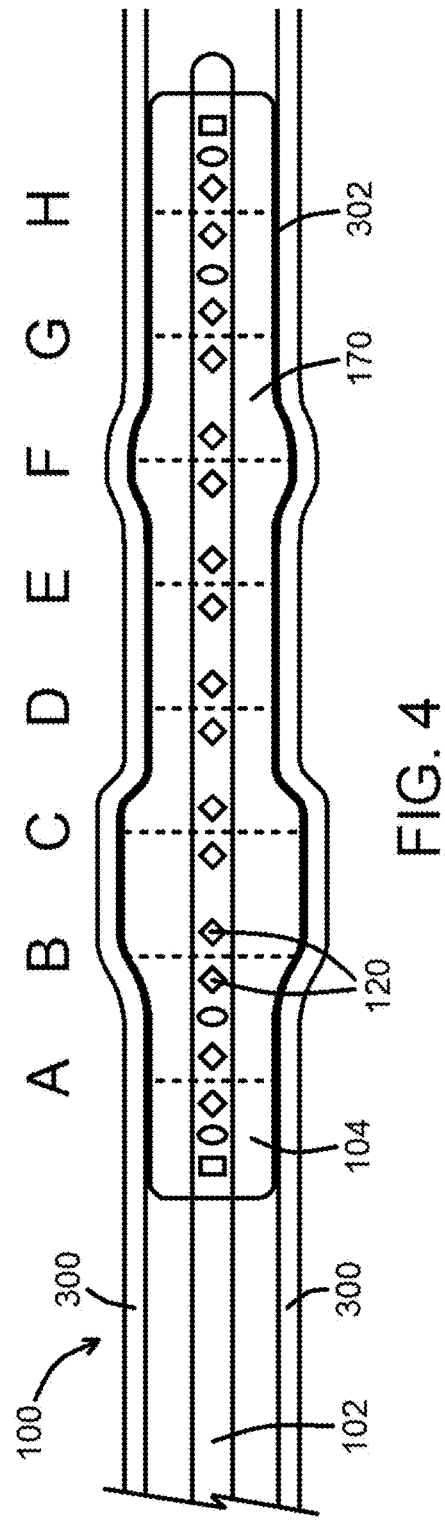

DEVICES, SYSTEMS, AND METHODS FOR DETERMINING VEIN GEOMETRIC AND COMPLIANCE PROFILES FOR VENOUS STENTING

PRIORITY

The present application is related to, and claims the priority benefit of, U.S. Provisional Patent Application Ser. No. 61/980,364 filed Apr. 16, 2014, the contents of which are incorporated into the present disclosure in their entirety.

BACKGROUND

Iliac vein stenting is a promising new approach to treat patients with a variety of chronic venous diseases. The stents currently used are prone to compression/migration of the upper end of the stent (at the iliac-caval junction, for example, which is a choke point) requiring reintervention in a significant number of cases (10-20%). These stent 'end effects' are particularly common when treating lesions at or near the iliac-caval junction and the stent is attempted to be placed 'precisely' at the junction to avoid stent encroachment of vena cava proper. Both primary and postthrombotic lesions occur frequently at this location.

Constriction of the stent diameter by as much as 30% can occur due to recoil in some lesions despite adequate pre-dilatation, leading to unpredictable stent length. It is also common to observe the upper end of the stent "squeezed" downward by a tight lesion and retracted axially.

Precise stent placement across this lesion is difficult, because of the variability of the lesion length, and also because of the anatomic variability of the arterial and venous bifurcations. Venography is the current standard for visualizing the anatomy of the vein but it is a poor guide to assess these variabilities.

Although intravascular ultrasound (IVUS) is more accurate than venography and provides local assessment of geometric complexities, it cannot assess the compliance of the vein (as it does not interrogate the vein under stent-like radial force conditions), and it is quite expensive and requires detailed training. Hence, there is a significant need for a technology that can assess the lumen profile, namely the variation in cross-sectional area (CSA) along the length of one or more veins, for example, along with the axial variation in the compliance of the veins (and radial force) to assess the degree of external compression on the vein of interest.

BRIEF SUMMARY

In at least one embodiment of a device of the present disclosure, the device comprises an elongated body configured to fit within a mammalian luminal organ, such as a vein, a balloon coupled to the elongated body, the balloon capable of and configured for inflation and deflation within the mammalian luminal organ, at least two excitation electrodes positioned along the elongated body within the balloon, and at least three detection electrodes positioned in between at least two of the at least two excitation electrodes, wherein when the elongated body is at least partially inserted into the mammalian luminal organ, and wherein when at least two of the at least two excitation electrodes generate an electric field, at least two of the at least three detection electrodes can detect the electric field and obtain at least one conductance measurement within the balloon. In another embodiment, the at least one conductance measurement is obtained in the presence of a fluid within the balloon. In yet another embodiment, a plurality of conductance measurements can be obtained within the balloon using at least two of the at least three detection electrodes. In an additional embodiment, the plurality of conductance measurements are indicative of various stages of balloon inflation.

In at least one embodiment of a device of the present disclosure, the device further comprises at least one pressure sensor and/or at least one temperature sensor. In an additional embodiment, the device is configured to obtain a plurality of conductance measurements, used to determine a plurality of cross-sectional areas, along a length of the balloon at various inflation pressures, which can be used to generate a profile of the balloon, corresponding to dimensions of the mammalian luminal organ. In an additional embodiment, the device further defines a suction/infusion port defined within the elongated body and in communication with a lumen defined within the elongated body. In another embodiment, the device forms at least part of an impedance system, the impedance system further comprising a data acquisition and processing system and/or a processor and/or a storage medium and/or a stent and/or an injection source.

In at least one embodiment of a device of the present disclosure, the elongated body is configured as a catheter or a wire. The present disclosure also includes disclosure of a device and/or a system, as described and/or shown herein.

In at least one embodiment of a method of the present disclosure, the method comprises an exemplary introduction step, an exemplary inflation step, and an exemplary measurement step. In another embodiment, the method further comprises an exemplary profile generation step and/or an exemplary stent placement step. In yet another embodiment, the exemplary stent placement step is used to place a stent within a mammalian luminal organ. In an additional embodiment, the stent can be selected, or even produced, to correspond to a patient's vessel compliance, so that portions of the stent can properly fit within the mammalian luminal organ and not migrate within and/or perforate the mammalian luminal organ. In yet an additional embodiment, a/the mammalian luminal organ comprises a vein, and wherein a/the stent is ultimately placed within the vein. In an additional embodiment, the method is performed to identify portions of a/the mammalian luminal organ that are relatively more or less compliant than other portions of the mammalian luminal organ.

In at least one embodiment of a method of the present disclosure, the exemplary measurement step includes obtaining one or more conductance measurements within a mammalian luminal organ using impedance electrodes positioned along an impedance device and optionally one or more pressure measurements using one or more pressure sensors of the impedance device and/or one or more temperature measurements using one or more temperature sensors of the impedance device. In another embodiment, the one or more temperature measurements are used with the one or more conductance measurements to determine one or more cross-sectional areas of the mammalian luminal organ. In yet another embodiment, the exemplary measurement step is performed in connection with inflation of a balloon of the impedance device. In an additional embodiment, the balloon is compliant so that pressures within the balloon due to inflation are transferred to the luminal organ.

The present disclosure also includes disclosure of a method, as described and/or shown herein.

In at least one embodiment of a device of the present disclosure, the device comprises an elongated body configured to fit within a mammalian luminal organ, a balloon coupled to the elongated body, the balloon capable of and configured for inflation and deflation within the mammalian luminal organ, at least two excitation electrodes positioned along the elongated body within the balloon, and a plurality of at least three detection electrodes positioned in between at least two of the at least two excitation electrodes, wherein when the elongated body is at least partially inserted into the mammalian luminal organ, and wherein when at least two of the at least two excitation electrodes generate an electric field, a first pair of two adjacent detection electrodes of the at least three detection electrodes can detect the electric field and obtain a first conductance measurement within the balloon, and a second pair of two adjacent detection electrodes of the at least three detection electrodes can detect the electric field and obtain a second conductance measurement within the balloon, the first conductance measurement and the second conductance measurement indicative of different locations within the balloon, and wherein the device is configured to obtain pressure data in addition to the first conductance measurement and the second conductance measurement, wherein dimensional data from the first conductance measurement or the second conductance measurement along with the pressure data provide compliance data at one or more locations within the mammalian luminal organ. In at least one device embodiment, the first conductance measurement and the second conductance measurement are obtained in the presence of a fluid within the balloon. In at least one device embodiment, a plurality of conductance measurements in addition to the first conductance measurement and the second conductance measurement can be obtained within the balloon using at least two of the at least three detection electrodes. In at least one device embodiment, the plurality of conductance measurements are indicative of various stages of balloon inflation.

In at least one embodiment of a device of the present disclosure, the device further comprises at least one additional element in communication with an inner lumen of the balloon, the at least one additional element selected from the group consisting of a pressure sensor and a temperature sensor. In at least one device embodiment, the device is configured to obtain a plurality of conductance measurements, used to determine a plurality of cross-sectional areas, along a length of the balloon at various inflation pressures, the plurality of conductance measurements used to generate a profile of the balloon, corresponding to dimensions of the mammalian luminal organ. In at least one device embodiment, the device further defines a suction/infusion port defined within the elongated body and in communication with a lumen defined within the elongated body.

In at least one embodiment of a device of the present disclosure, the device forms least part of an impedance system, the impedance system further comprising a data acquisition and processing system. In at least one device embodiment, the data acquisition and processing system is configured to display the first conductance measurement and the second conductance measurement in real time. In at least one device embodiment, the plurality of at least three detection electrodes comprises a plurality of at least seven detection electrodes forming six consecutive adjacent pairs of detection electrodes. In at least one device embodiment, the plurality of at least three detection electrodes comprises a plurality of at least seventeen detection electrodes forming sixteen consecutive adjacent pairs of detection electrodes.

In at least one embodiment of a method of the present disclosure, the method comprises the steps of inserting at least part of a device into a mammalian luminal organ, the device comprising an elongated body configured to fit within the mammalian luminal organ, a balloon coupled to the elongated body, the balloon capable of and configured for inflation and deflation within the mammalian luminal organ, at least two excitation electrodes positioned along the elongated body within the balloon, and a plurality of at least three detection electrodes positioned in between at least two of the at least two excitation electrodes, inflating the balloon within the mammalian luminal organ so that the balloon contacts the mammalian luminal organ, obtaining a first conductance measurement within the balloon by exciting an electric field using the at least two excitation electrodes and detecting the electric field using a first pair of two adjacent detection electrodes, and obtaining a second conductance measurement within the balloon by detecting the electric field using a second pair of two adjacent detection electrodes different from the first pair of two adjacent detection electrodes, the first conductance measurement and the second conductance measurement indicative of different locations within the balloon. In at least one method, the method further comprises the step of generating a profile of the mammalian luminal organ based upon the first conductance measurement and the second conductance measurement. In at least one method, the method further comprises the steps of selecting an appropriately sized stent based upon the profile, and placing the appropriately-sized stent within the mammalian luminal organ. In at least one method, the profile indicates a lesion or other vascular abnormality within the mammalian luminal organ, and wherein the placing step is performed to place the appropriately-sized stent within the mammalian luminal organ at the lesion or other vascular abnormality. In at least one method, the mammalian luminal organ is a vein, and wherein the stent is ultimately placed within the vein.

In at least one embodiment of a method of the present disclosure, the method is performed to identify portions of/the mammalian luminal organ that are relatively more or less compliant than other portions of the mammalian luminal organ. In at least one method, at least one of the steps of obtaining a first conductance measurement and obtaining a second conductance measurement is performed in connection with obtaining at least one pressure measurement and/or at least one temperature measurement within the balloon.

In at least one embodiment of a method of the present disclosure, the method comprises the steps of inserting at least part of a device into a mammalian luminal organ, the device comprising an elongated body configured to fit within the mammalian luminal organ, a balloon coupled to the elongated body, the balloon capable of and configured for inflation and deflation within the mammalian luminal organ, at least two excitation electrodes positioned along the elongated body within the balloon, and a plurality of at least five detection electrodes positioned in between at least two of the at least two excitation electrodes, inflating the balloon within the mammalian luminal organ at a lesion or other vascular abnormality so that the balloon contacts the mammalian luminal organ, obtaining at least four conductance measurements within the balloon by exciting an electric field using the at least two excitation electrodes and detecting the electric field using a first pair of two adjacent detection electrodes, a second pair of two adjacent detection electrodes, a third pair of two adjacent detection electrodes, and a fourth pair of two adjacent detection electrodes, each of the four conductance measurements indicative of different locations within the balloon, generating a profile of the mammalian luminal organ based upon the at least four conductance measurements, the profile identifying a location of the lesion or other vascular abnormality relative to the balloon and a size of the lesion or other vascular abnormality relative to other portions of the mammalian luminal organ, identifying an appropriately-sized stent based upon the size of the lesion or other vascular abnormality, and placing the stent within the mammalian luminal organ at the location of the lesion or other vascular abnormality identified by the profile. In at least one method, the step of obtaining at least four conductance measurements is performed in connection with obtaining at least one pressure measurement and/or at least one temperature measurement within the balloon.

BRIEF DESCRIPTION OF THE DRAWINGS

The disclosed embodiments and other features, advantages, and disclosures contained herein, and the matter of attaining them, will become apparent and the present disclosure will be better understood by reference to the following description of various exemplary embodiments of the present disclosure taken in conjunction with the accompanying drawings, wherein:

FIGS. 1 and 2 show impedance devices with balloons, according to exemplary embodiments of the present disclosure;

FIGS. 3 and 4 show impedance devices within a mammalian luminal organ, according to exemplary embodiments of the present disclosure;

Figure 5A:
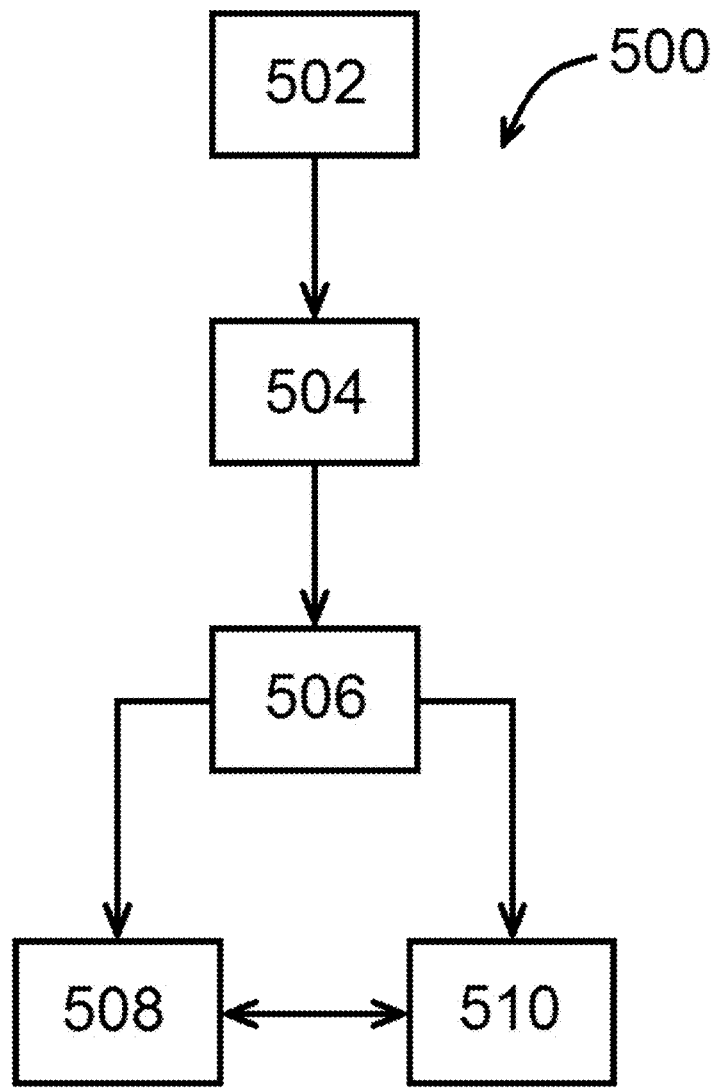
FIG. 5A shows a block method step diagram, according to an exemplary embodiment of the present disclosure.

An overview of the features, functions and/or configurations of the components depicted in the various figures will now be presented. It should be appreciated that not all of the features of the components of the figures are necessarily described. Some of these non-discussed features, such as various couplers, etc., as well as discussed features are inherent from the figures themselves. Other non-discussed features may be inherent in component geometry and/or configuration.

DETAILED DESCRIPTION

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

A distal portion of an exemplary device of the present disclosure is shown in FIG. 1. As shown in FIG. 1, an exemplary device 100 comprises an elongated body 102 and a balloon 104 positioned thereon. Within balloon 104, at least two excitation electrodes 106, 108, capable of generating an electric field within balloon 104, are positioned within balloon 104, such as being coupled to elongated body 102. A plurality (three or more) of detection electrodes 120 are also positioned within balloon, such as also being coupled to elongated body 102, and are positioned in between excitation electrodes 106, 108. As discussed in further detail herein, detection electrodes 120 are configured to detect the electrical field generated by excitation electrodes 106, 108, such as when a fluid is placed within balloon 104, allowing a user of device 100 to obtain various impedance measurements for use at least as described herein.

Exemplary devices 100 of the present disclosure, as referenced herein, also comprise at least one pressure sensor 150 and at least one temperature sensor 152, such as a thermistor, for example. Use of temperature measurements, as provided in further detail herein, can help provide accurate conductance measurements given that conductance is a linear function of temperature. Said devices 100, configured as described herein, can be used to obtain a plurality of conductance measurements, used to determine a plurality of cross-sectional areas (CSAs) (referred to herein as exemplary geometries), along a length of the balloon 104 at various inflation pressures, which can be used to generate a profile of the balloon 104, corresponding to dimensions of a luminal organ 300, as provided in further detail herein. Said devices 100 can provide, for example, diagnostic information to inform optimal stent deployment and treatment.

Exemplary devices 100 of the present disclosure, such as shown in FIG. 1, would also include a suction/infusion port 140 defined within elongated body 102 and in communication with a lumen 112 defined within elongated body 102. Suction/infusion port 140 would be defined within elongated body 102 within balloon 104, so that fluid 170 from a fluid source (not shown in FIG. 1), such as a syringe, into and through lumen 112 of elongated body 102, and into balloon 104, via a suction/infusion port 140 defined within elongated body 102 within balloon 104. Fluid 170 and/or a gas (such as air) can also be removed from balloon 104 via suction/infusion port 140. Fluid 170 can also be saline or another fluid having a known conductivity so that detection electrodes 120 can obtain impedance measurements within balloon 104 in the presence of said fluid 170.

FIG. 2 shows another embodiment of an exemplary device 100 of the present disclosure, configured as a wire (another exemplary elongated body 102) having a balloon 104 positioned thereon. Such an embodiment may be desired in situations where wires of a particular stiffness and/or flexibility are desired. In such an embodiment, device 100 would further comprise an inflation tube 200 coupled to balloon 104, so that a fluid 170 can be delivered into and removed from balloon 104, as desired, by introducing fluid 170 into inflation tube 200 and into balloon 104 via a suction/infusion port 140 defined within balloon 104 or removing fluid from balloon 104 through inflation tube 200, respectively.

A controlled increase in pressure (also referred to herein as a pressure ramp) can be used along with saline (an exemplary fluid 170 used to fill balloon 104) to simultaneously record multiple CSA measurements along a length of balloon 104 inside the vein (an exemplary luminal organ 300) of interest. FIG. 3 shows an exemplary device 100 of the present disclosure positioned within a vein (an exemplary luminal organ 300), with relatively low to moderate internal balloon 104 pressure by way of balloon 104 inflation using fluid 170. As shown in FIG. 3, an outer perimeter 302 of balloon 104 contacts luminal organ 300, but does not deform luminal organ 300, due to the relatively low to moderate internal balloon 104 pressure. FIG. 4 shows the same device 100 with additional internal balloon 104 pressure due to additional fluid 170 within balloon 104. As shown in FIG. 4, luminal organ 300 has deformed in various locations, which is indicative of luminal organ 300 being relatively more compliant, and therefore more susceptible to stretching, at those locations. Locations A, B, C, D, E, F, G, and H are identified in FIG. 4 as being locations between pairs of detection electrodes 120 (such as labeled in FIGS. 1 and 2, and as labeled in connection with location B in FIG. 4). As shown in FIG. 4, for example, an exemplary luminal organ 300 is more compliant at locations B, C, and F, for example, as compared to locations A, D, E, G, and H. Impedance measurements can be obtained at each location, and potentially between any two detection electrodes 120 along elongated body 102, and those impedance measurements can be used to determine CSA, as noted below.

With reference to the embodiments shown in FIGS. 1-4 for example, and using the same to obtain impedance measurements within a balloon 104 filled with fluid 170 (such as saline), said devices 100 can be used consistent with the disclosure of U.S. Pat. No. 8,114,143 to Kassab et al. and U.S. Pat. No. 8,406,867 to Kassab, for example, the contents of which are incorporated herein by reference. However, with the embodiments referenced herein, (σ) multiple cross-sectional areas can be obtained between any number of the plurality of detection electrodes 120, (b) multiple pressures within balloon 104 can be obtained using one or more pressure sensors 150, so to correlate CSAs with pressure at various locations along elongated body 102 within balloon 104 (as noted in further detail below), (c) multiple temperatures within balloon 104 can be obtained using one or more temperature sensors 152, so to correlate CSAs with temperature at various locations along elongated body 102 within balloon 104 (as noted in further detail below) and correct for variations in impedance, and thus CSA, based upon temperature, and (d) vessel (luminal organ 300) compliance at various locations can be obtained using a single device 100.

Various exemplary embodiments of devices 100 of the present disclosure may be used to obtain multiple CSAs within balloon 104, at various known pressures and temperatures, as follows. In at least one embodiment of a method 500 to size a luminal organ of the present disclosure, as shown in the step diagram shown in FIG. 5A, the method comprises the steps of introducing at least part of an exemplary device 100 of the present disclosure into a luminal organ 300 (an exemplary introduction step 502), wherein device 100 comprises excitation electrodes 106 and 108 positioned along elongated body 102 within balloon 104, with three or more detection electrodes 120 positioned in between excitation electrodes 106, 108, along with one or more pressure sensors 150 and/or one or more temperature sensors 152 positioned along elongated body 102 within balloon 104. An exemplary method 502 then comprises the steps of inflating balloon 104 using fluid 170 (an exemplary inflation step 504), and obtaining one or more pressure measurements (using one or more pressure sensors 150) and/or one or more temperature measurements (using one or more temperature sensors 152) at or near the time of obtaining one or more impedance measurements using detection electrodes 120 (an exemplary measurement step 506) within balloon 104 upon excitation of excitation electrodes 106, 108 to generate an electric field. As referenced herein, the one or more temperature sensors 152 can be used to obtain one or more temperature measurements in connection with one or more conductance measurements, so that any calculation based upon the one or more conductance measurements, such as one or more CSAs, can be corrected due to the linear relationship between conductance and temperature. In view of the same, a clinician would not need to wait for the fluid 170 inside the balloon 104 to reach a certain temperature, and a fluid heating/cooling source would not be necessary.

In various embodiments, balloons 104 are compliant and of excess surface area or diameter than the vein (or other luminal organ 300) of interest in order to both conform to the shape of the lumen of the vein or other luminal organ 300 and to transmit the entire pressure to the wall of the vein or other luminal organ 300 such that balloon 104 does not take up the tension. Safety is still ensured with such a configuration, as inflation pressures are maintained at relatively low levels (such as at or under 200 mmHg), which is far below the rupture pressure of veins and other luminal organs 300.

Figure 5B:
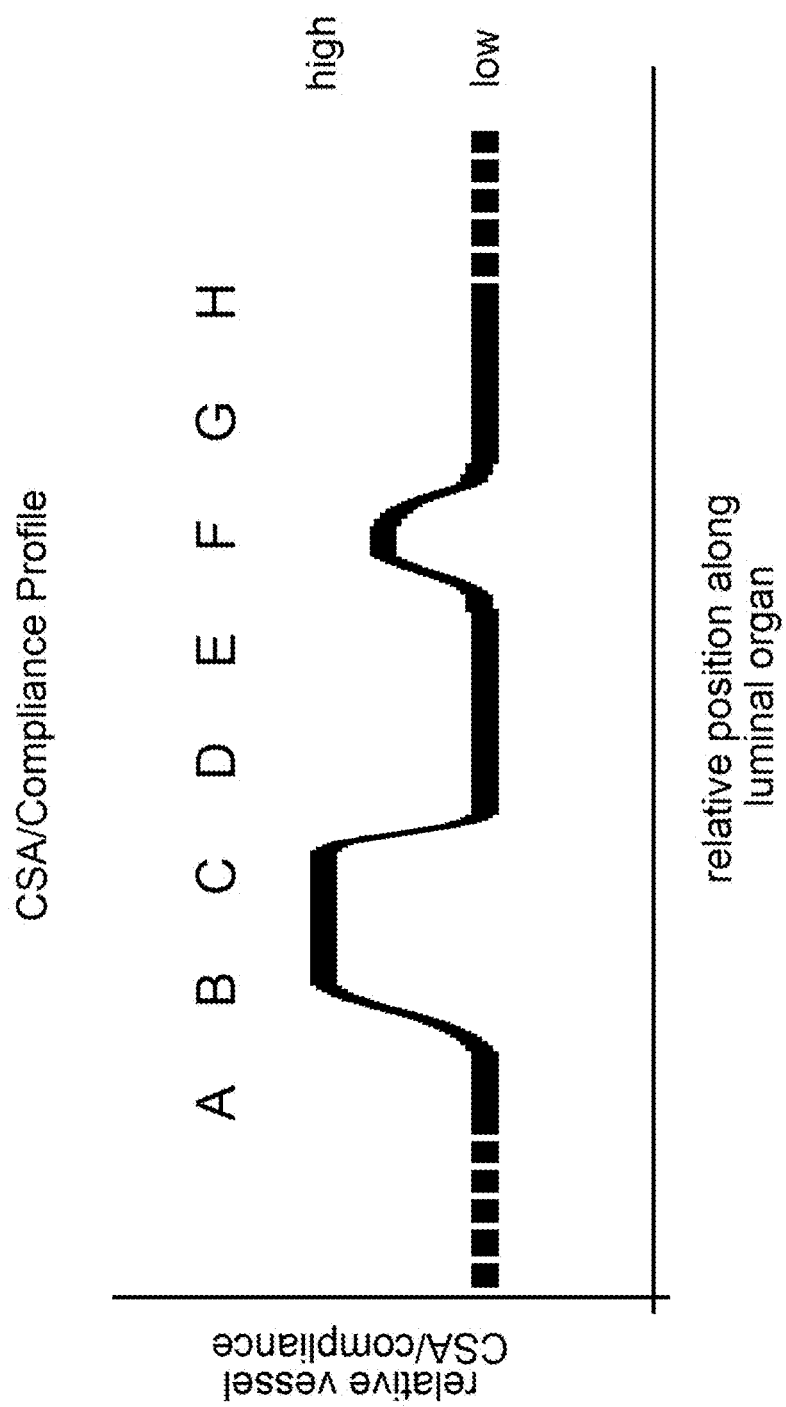
FIG. 5B shows a cross-sectional area/compliance profile, according to an exemplary embodiment of the present disclosure.
Figure 6:
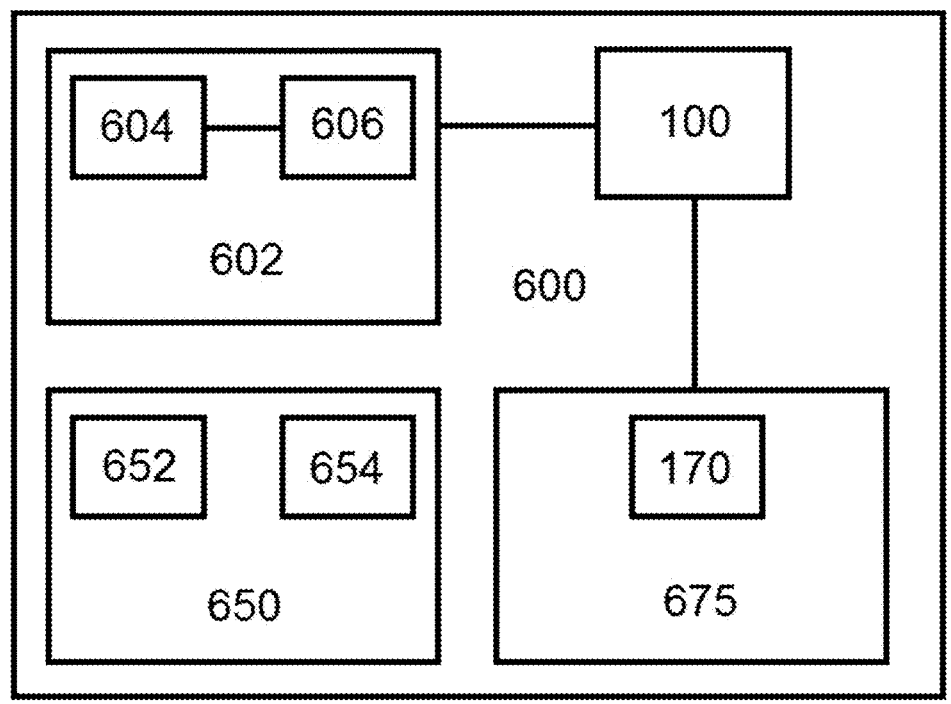
FIG. 6 shows a block component diagram of a system, according to an exemplary embodiment of the present disclosure.

The various measurements can then be used to generate multiple CSAs at various locations along elongated body 102 within balloon 104 and/or to be directly or indirectly used to generate a profile of relative vessel compliance (as corresponding to different CSAs) as shown in FIG. 5B, with letters A-H corresponding to positions A-H shown in FIG. 4 (an exemplary profile generation step 508). Regardless of profile generation, use of various devices 100 of the present disclosure can then also be used to determine dimensions of an appropriately-sized and configured stent 650 for potential use within the luminal organ 300 at or near the location of the aforementioned measurements (an exemplary stent placement step 510). Stent 650 can be selected, or even produced to correspond to a patient's vessel compliance, so that portions of stent 650 can properly fit within luminal organ 300 and not migrate within and/or perforate luminal organ 300. For example, a first stent portion 652, as shown in FIG. 6 referenced in further detail below, can be configured to correspond to a first vessel location (such as any of letters A-H referenced herein), and a second stent portion 654 can be configured to correspond to a second vessel location (such as any of the other letters A-H referenced herein not corresponding to the first vessel location). For example, first stent portion 652 could be relatively smaller in cross-section than second stent portion 654 after expansion/deployment, such as first stent portion 652 corresponding to any of letters A, D, E, G, and/or H in FIG. 4, and such as second stent portion 654 corresponding to any of letters B, C, and/or F in FIG. 4. In view of the foregoing, various devices 100 and/or systems 600 (referenced below) can be used in connection with various methods 500 of the present disclosure to interrogate the vein (an exemplary luminal organ 300) under stent-like radial force conditions to obtain luminal organ 300 information/data as generally referenced herein. The various devices 100, systems 600, and methods 500 of the present disclosure can assess the lumen profile, namely the variation in CSA along the length of one or more luminal organs 300, for example, along with the axial variation in the compliance of the veins (and radial force) to assess the degree of external compression on the luminal organs 300 of interest.

FIG. 6 shows a block diagram of certain components referenced herein (with device 100 and one or more other components comprising an exemplary impedance system 600 of the present disclosure), with an exemplary device 100 coupled to an exemplary data acquisition and processing system 602 (such as a computer or console, having a processor 604 operably coupled to a storage medium 606, so that data (measurements, for example) from device can be provided to data acquisition and processing system 602, processed using processor 604 and stored in storage medium 606 (such as a flash drive or hard disk drive, for example), and if desired, a stent 650 can be used by placing the same within a luminal organ 300, as referenced in U.S. Pat. No. 8,406,867 to Kassab, for example, using device 100 for example (re-inserting device 100 with stent 650 positioned thereon and re-inflating balloon 104 to expand stent 650, with the re-inflation being optionally corresponding to one or more of the original balloon 104 inflations to obtain the impedance measurements, for example. A fluid source 675 (such as a syringe or other vessel suitable for retaining fluid 170) is also shown as being connected to device 100, so that fluid 170 from fluid source 675 can be delivered to and from balloon 104.

Data from exemplary devices 100/systems 600 of the present disclosure are founded on a physical law of electricity (Ohm's Law) which provides a predictive and highly accurate basis for how balloon 104 (i.e., venous lesion when balloon 104 is inflated at said lesion) dimension is measured during venoplasty. Exemplary devices 100 of the present disclosure, as generally referenced herein, contain two excitation electrodes 106, 108 (and/or two radiopaque outer electrodes 750, as referenced in further detail herein on the outer edge of balloon 104) that inject a constant current (I) between them inside balloon 104. Exemplary devices 100 can contain several sets of detection electrode 120 (such as five detection electrodes 120 forming four successive pairs of detection electrodes 120, seven detection electrodes 120 forming six successive pairs of detection electrodes, 120, seventeen detection electrodes 120 forming sixteen sets of electrode pairs 120, or more or fewer detection electrodes (n) forming n−1 successive pairs of detection electrodes 120 in-between these outer electrodes 106, 108 (or 750), and each detection electrode pair 120 measures a variable voltage drop (V) inside balloon 104 as well as the conductivity of the solution (σ) within balloon 104 used for inflation.

The ratio of the constant current and variable voltage between any of the electrode pairs (i) is the total conductance for each electrode pair set ($G_i$=I/V). When inflated, Ohm's Law (Equation 1 noted below) states that the total measured conductance at any electrode pair (i) inside the balloon 104 ($G_i$) is related to the local inner cross-sectional area ($CSA_i$) of balloon 104, the electrical conductivity (σ) of the saline/contrast mixture used to inflate balloon 104, and the spacing between the measurement (detection) electrodes 120 (L) is given by Ohm's Law:

$$G_i = I/V = CSA_i * \sigma / L \quad [1]$$

The $G_i$ value is measured across each $i_{th}$ electrode pair and displayed by the console (data acquisition and processing system 602), σ is determined for the fluid injected inside balloon 104 (mixture of saline/contrast) in real time as described above, and L is a known constant (the fixed spacing between inner electrodes; L=1.0 mm, 1.1 mm, or another known/desired spacing). $CSA_i$ as well as effective balloon 104 circular diameter can be determined for any area regardless of shape or geometry (similar to CT measurements), and is calculated by solving Equation 1 and adding twice the wall thickness (wt) of the balloon 104 as:

$$\text{Diameter}_o = \sqrt{(4*G_i*L/(\pi*\sigma))} + 2*wt \quad [2]$$

Figure 9A:
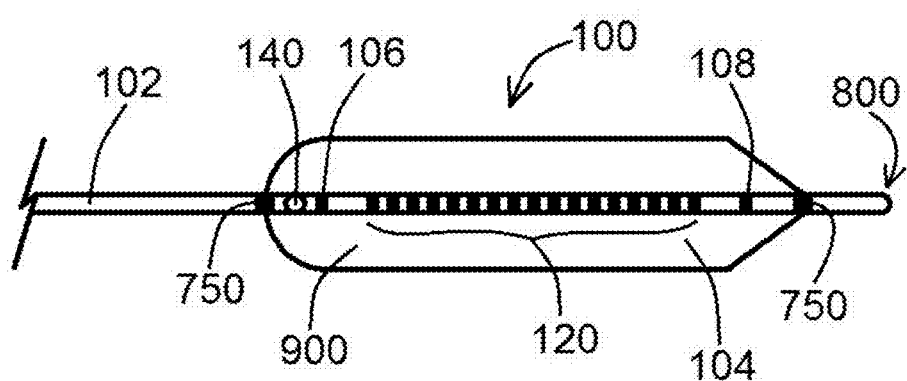
FIG. 9A shows a portion of an exemplary device having a balloon with a plurality of detection electrodes therein, according to an exemplary embodiment of the present disclosure.
Figure 9B:
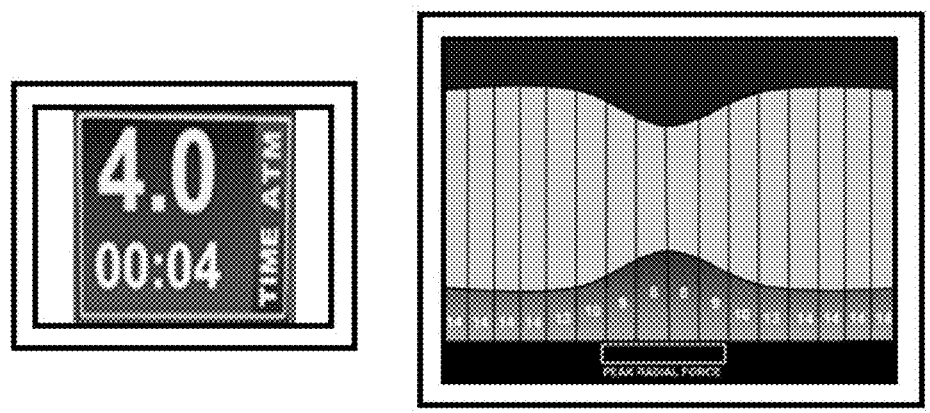
FIG. 9B shows exemplary screenshots from a data acquisition and processing system, according to exemplary embodiments of the present disclosure.

Since all other variables are known, Equation 2 shows that the balloon 104 size is directly proportional to $G_i$. Given the continuous $G_i$ measurement on the console, Equation 2 can be instantaneously solved and the diameter/CSA, compliance (ΔCSA/ΔP) as well as radial force (P*CSA) displayed on the console to provide real-time feedback on lesion size as well as morphology and distensibility (such as shown in FIG. 9B). Although $G_i$ is the main variable that relates directly to CSA, the value of σ can sometimes vary and impact system accuracy. The σ term expresses the inherent ability of the fluid inside balloon 104 to conduct electricity and varies based on the temperature and type of fluid inside balloon 104. The variability in the saline/contrast solutions prepared by the physician or other personnel are taken into account by exciting and detecting with closely spaced electrodes. Specifically, Equation 1 states that the measured conductance (G) is equal to the fluid conductivity (σ) when the ratio of cross-sectional area to electrode spacing (i.e., CSA/L) tends to 1. The optimized excitation/detection spacing of 1.1 mm provides a spherical electrical field and the measured conductance is equal to the conductivity of the saline/contrast mixture (regardless of mixture prepared by the clinician at the time of the procedure). This approach allows for simultaneous determination of conductivity, conductance, and hence, accurate real-time CSA while removing variability associated with saline/contrast mixing and any temperature variations (room temperature solution to body temperature) during inflation.

A modified version of Ohm's law may be used, namely:

$$CSA = (G/L)/\alpha(T) \quad [3]$$

wherein CSA is the cross-sectional area of balloon 104 at a particular location (such as between two selected detection electrodes 120 among the plurality of detection electrodes), G is the electrical conductance given by a ratio of current and voltage drop (I/V, wherein I represents injected current and V is the measured voltage drop along detection electrodes 120), L is a constant for the length of spacing between selected detection electrodes 120 of device 100, T is temperature, and α is the electrical conductivity of the fluid 170 (such as saline or a saline/contrast mixture) within balloon 104, which depends on temperature in a linear fashion. Equation [3] can then be used to provide CSA in real time given the conductivity of fluid 170 used to inflate the balloon 104 (such as, for example, half normal saline (0.9% NaCl)) and/or quarter or half contrast (iodine, etc.), or another fluid 170 useful to obtain conductance measurements as generally referenced herein. As noted above, the use of temperature, such as obtained using a temperature sensor 152 within a luminal organ 300, can be used to accurately determine the conductances and related CSAs since conductance is a linear function of temperature. This would allow more accurate CSA determinations, as balloon 104 can be inflated with fluid 170 at room temperature or another temperature, which then heats up to body temperature within luminal organ 300. During fluid 170 infusion, fluid 170 is at a temperature between room (or other original temperature) and body temperature, and thus knowledge of fluid temperature 170 when obtaining conductance measurements allows for an accurate determination of conductance, and thus an accurate determination of CSA.

Device 100 embodiments of the present disclosure have several advantages. First, all electrodes (106, 108, and 120) are positioned along elongated body 102 within balloon 104, so minimal risk to damage of said electrodes 106, 108, 120 arises. This does not preclude devices 100 from having electrodes outside of balloon 104, but applies to device 100 embodiments that only have electrodes within balloon 104. Second, and since balloon 104, in various embodiments, insulates the electric field generated by excitation electrodes 106, 108, there is no parallel conductance and hence no need for multiple fluid 170 injections to obtain a desired impedance measurement. In addition, said devices 100 incorporate the ability to size a luminal organ 300 at multiple locations and optionally also deliver a stent 650 as referenced herein. Using Equation [3] for example, real-time measurements of CSA can be obtained as desired, with no additional procedures required by a physician. The sizing results are quite accurate, providing additional confidence of the sizing measurements without the need for echocardiograms, MRIs, or other expensive imaging mechanisms.

As referenced above, and in addition to obtaining CSA/compliance profiles (multiple CSAs along elongated body 102 between detection electrodes 120, which can be used to generate a profile of CSA/compliance on one axis and relative position/distance on the other (distance being based upon known distances between detection electrodes 120 and the number of detection electrodes 120 used to obtain the impedance measurements providing CSA)), such data can be used to construct pressure-CSA (P-CSA) relations at multiple points along the length of the vein (an exemplary luminal organ 300). The luminal organ/vessel compliance can then be computed from the P-CSA relation as the change of CSA per change of P as the standard definition (or, to normalize compliance by the reference CSA at in vivo pressure, for example). Radial forces can also be displayed, which are generally the pressures (measured by the pressure sensor(s) 150), multiplied by the area (which can be measured using the various impedance electrodes of device 100), which would inform the degree of radial force required by the stent 650.

This data can inform the stenting procedure by assessing the axial variation of dimensions of the vein, for example, and the degree of external compression on the vein. This allows the clinician to impose greater radial stent forces at desired locations, lesser radial stent forces at other desired locations, to provide an isodiametric stent that prevents stenosis/restenosis and migration, as generally referenced herein.

Exemplary devices 100, systems 600, and methods 500 of the present disclosure can provide both a sizing profile along the balloon 104 and compliance information (i.e., pressure-CSA relation of the vein (luminal organ 300) of interest) to determine the stent 170 size/dimensions/configuration as well as the degree of compression noted above. This also allows real time digital information on the profile of the balloon 104 (i.e., CSA at various axial points of the balloon 104; i.e., the CSA at the iliac-caval unction (choke point) may be reflected by a smaller CSA than other portions of the balloon 104).

Figure 7:
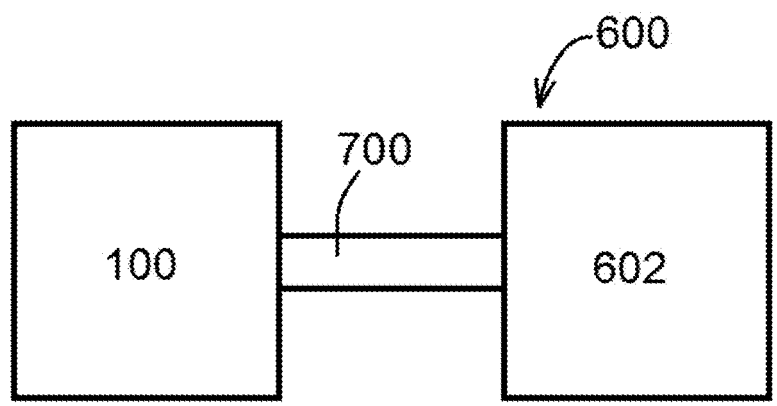
FIG. 7 shows a block component diagram of portions of a system, according to an exemplary embodiment of the present disclosure.
Figure 8:
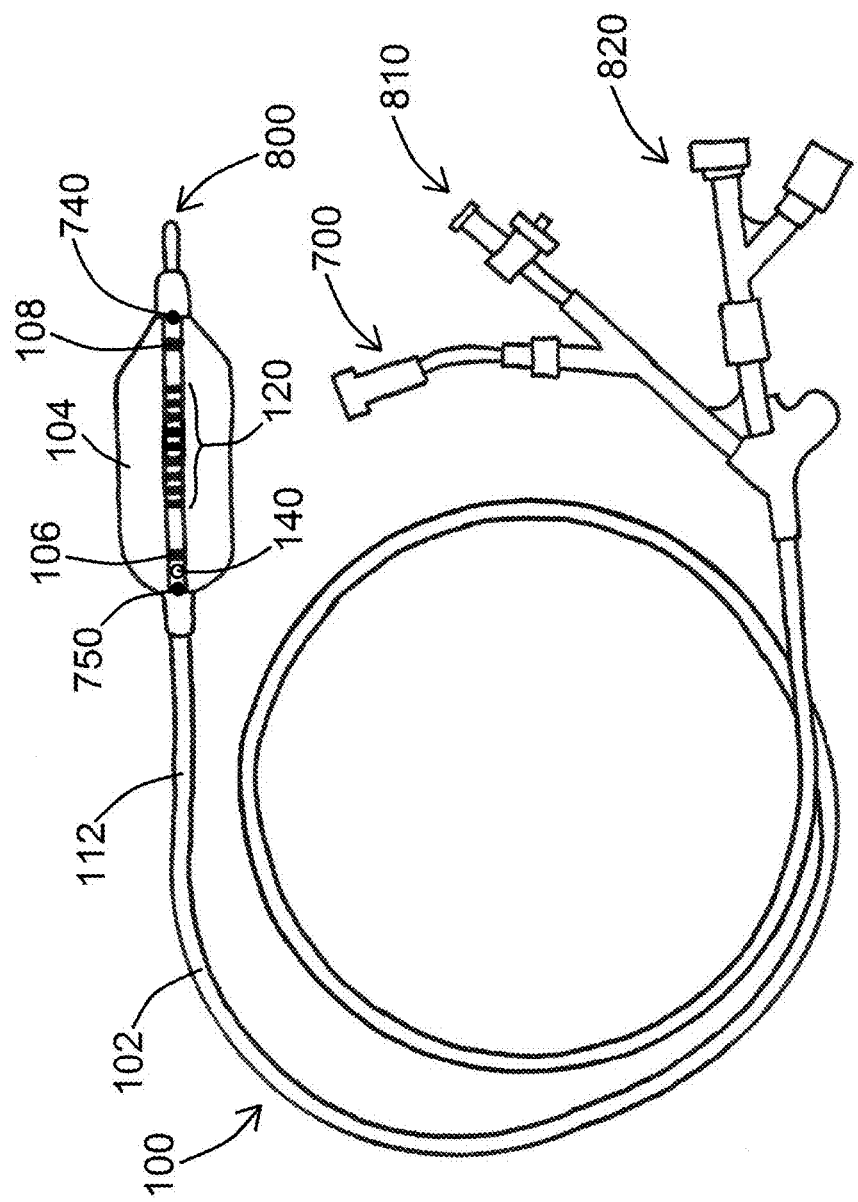
FIG. 8 shows an exemplary device having a balloon with a plurality of detection electrodes therein, according to an exemplary embodiment of the present disclosure.

An exemplary system 600 of the present disclosure is described as follows. As shown in FIG. 7, an exemplary system 600 comprises a device 100 and a data acquisition and processing system 602, whereby device 100 connects to data acquisition and processing system 602 via, for example, a connector 700. Device 100, in the present example and as shown in greater detail in FIG. 8, comprises an elongated body 102 (configured as a balloon catheter) having a 5 French diameter, 140 cm length, and a 70 mm long semi-compliant balloon 104 coupled to elongated body 102. Balloon 104, in such an example, has a 2-18 mm diameter, meaning that balloon 104 diameters range from 2-18 mm depending on the application, with a set of optional radiopaque outer electrodes 750 that mark/identify the relative edges of balloon 104. Radiopaque outer electrodes 750 can also be used to stimulate a constant current between them (similar to excitation electrodes 106, 108) as may be desired. Elongated body 102 (the catheter part of system 600) defines a lumen 112 therein so to allow for 0.035" over-the-wire exchange, such as when a wire (not shown) is advanced into the vasculature and parts of system 100 are then advanced over the wire. A suction/infusion port 140 (also referred to as a proximal port) can be used for balloon 104 inflation and optional pressure monitoring within balloon 104 (such as when a pressure sensor 150 is not used). FIG. 8 also shows other elements coupled to, in communication with, or formed as part of, elongated body 102 of an exemplary device 100 of the present disclosure, such as, for example, a connector 700 (used to connect device 100 to data acquisition and processing system 602), inflation portion 810 (configured to facilitate inflation and deflation of balloon 104), and a wire exchange portion 820, configured so that device 100 can be advanced over a wire (not shown) previously inserted into the vasculature.

In various embodiments, the electric current stimulated within balloon 104 is an alternating 136 µApp, 10 kHz waveform, which is known to be safe when stimulated directly within the vasculature. During balloon 104 inflation and deflation, additional sets of sixteen (16) detection electrodes 120 (or more or less sets of detection electrodes 120, such as shown in the partial device 100 view in FIG. 9A) in between the outer electrodes (excitation electrodes 106, 108, for example) are spaced ~1 mm apart (the width of each detection electrode 120 is 1 mm) and make the balloon 104 sizing and solution conductivity measurements. As shown in FIG. 9A, and in the center of balloon 104, there is a row of seventeen (17) electrodes 120, which make up sixteen (16) pairs of electrodes 120 when grouping them in successive pairs. The multiple measurements made inside the balloon 104 profile can be used to locate a minimum diameter during inflation which corresponds to the venous lesion, for example, and a reference diameter of the vessel. Thus, instead of having just one set of electrodes 120 in the middle of the balloon 104 and requiring the physician or other medical personnel to place and maintain these electrodes 120 in the center during inflation (so to introduce fluid into balloon lumen 900 of balloon 104), the device 100 has multiple electrode 120 pairs along the length of the balloon 104 so that the physician or other medical personnel does not have to precisely place the middle of the balloon 104 in the venous lesion during inflation (although this is still recommended).

Additional functionality of device 100 (also referred to as a peripheral venous balloon (PVB) device) is provided through integration of the balloon 104 pressure (a conventionally obtained measurement) into the data acquisition and processing system 602 for determination and display of pressure, compliance and radial force. A sterile connector cable (not shown) easily attaches to the proximal electrode connector of the PVB and the display console (data acquisition and processing system 602). For example, and as shown in the exemplary screenshots in FIG. 9B, a data acquisition and processing system 602 (such as a computer or console) can display pressure, time, and peak radial force data, for example. Data acquisition and processing system 602 can also a) generate the current across excitation electrodes 106, 108 (and/or radiopaque outer electrodes 750, as may be desired), b) measure voltage drops across the various pairs of detection electrodes 120), c) calculate various balloon 104 sizes (cross-sectional areas) as referenced herein, and/or d) display the results in real time to the user.

As shown in FIG. 9B, relatively narrow portions of a vein (or other vessel/luminal organ) can be identified from the profile comprising CSAs within balloon 104. A lesion, choke point (such as caused by an artery resting on the vein, compressing the vein), or other abnormality within the vessel can not only be identified (as existing or not), but can also be located via its relative positioning to balloon 104. For example, when device 100 is inserted into a vasculature, the user positioning the device 100 knows the location of balloon 104 within the vasculature, for example, based upon an amount (length) of elongated body 102 inserted into the vasculature. In one example, if a 70 mm long balloon 104 positioned upon a 140 cm long device 100 is inserted 100 cm into the vasculature and operated as referenced herein identifying a lesion, choke point, or other abnormality within the vasculature from the profile, a precise location and relative size/dimensions of the lesion, choke point, or other abnormality can be identified based upon the profile, the length of the balloon 104, and the amount (length) of device 100 inserted into the vasculature.

It is further noted that as shown in FIGS. 5B and 9B, the location, dimensions, size, etc., of the lesion, choke point, or other abnormality within the vasculature can be made by inflating the balloon 104 and obtaining conductance measurements as referenced herein without needing to subsequently move balloon 104 to another location. As noted above, should the profile identify the lesion, choke point, or other abnormality within the vasculature, the desired information has been obtained. If the profile does not identify the location/dimensions of the lesion, choke point, or other abnormality within the vasculature, device 100 can of course be moved distally or proximally and operated again as noted herein to potentially identify the lesion, choke point, or other abnormality within the vasculature.

As referenced herein, various pieces of information can be obtained by way of operating devices 100/systems 600 of the present disclosure including, but not limited to, CSAs, compliance (using CSA and pressure information), and radial force (also using CSA and pressure information). While multiple CSAs can be obtained within the balloon 104 at different locations along the length of balloon 104 without moving balloon 104, only one pressure sensor 150 in communication with balloon lumen 900 is needed to obtain the pressure measurements. Compliance and/or radial force information can be used not only to select an appropriately-sized stent 650, as generally referenced herein, but can also be used in connection with the potential generation/manufacture of one or more stents 950 for a particular patient vasculature, providing a "personalized medicine" approach to vascular condition treatment. For example, and as shown in FIG. 5B, the CSA/compliance curve identifies portions of the vessel that are more compliant than others. Similarly, a profile can also depict radial force data, which would inform the degree of radial force required by the stent 650. A stent 650 can then be developed corresponding to the compliance and/or radial force information so to exert the appropriate forces against the vessel at the appropriate locations along the same.

In various embodiments, device 100 components are bio-compatible and provided sterile to the clinician.

Figure 10A:
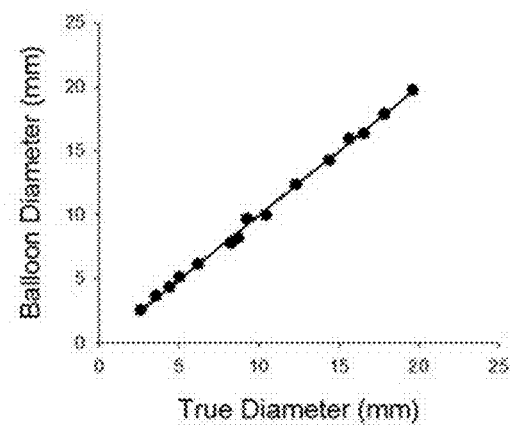
FIG. 10A shows a graph of balloon diameter to true diameter, according to an exemplary embodiment of the present disclosure.
Figure 10B:
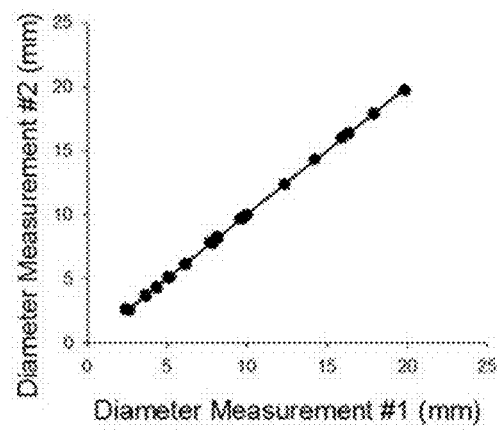
FIG. 10B shows a graph comparing two diameter measurements within cylindrical phantoms, according to an exemplary embodiment of the present disclosure.
Figure 10C:
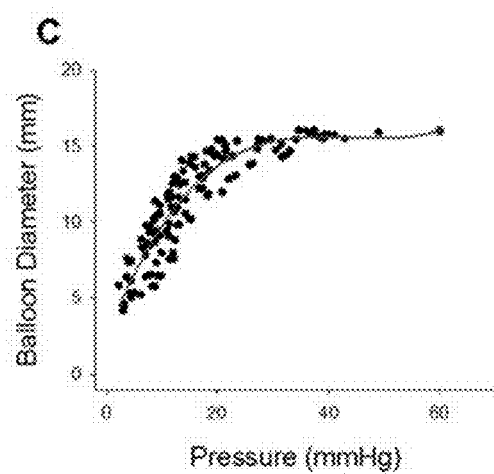
FIG. 10C shows a graph of balloon diameter to pressure, demonstrating the ability to determine venous compliance (the change in diameter divided by the change in pressure) according to an exemplary embodiment of the present disclosure.

An exemplary device 100 of the present disclosure was used for sizing on the bench and in vivo, demonstrating accurate and repeatable sizing results across a full range of possible venous diameters as shown in FIG. 10A. Device 100 measurements were made in circular and non-circular 2-20 mm diameter phantoms on the bench, while in vivo measurements were made in common iliac and jugular veins in healthy swine (n=3). Accuracy was determined by comparing device 100 measurements to the known dimension (bench). Overall repeatability was determined by comparing consecutive repeat device 100 measurements to each other. Bench and in vivo results were excellent with an average accuracy root mean square (RMS) error of 1.71% and repeatability accuracy of 0.91%, as shown in FIG. 10B. There was a small and clinically insignificant difference for the accuracy and repeatability measurements (accuracy difference=−0.04±0.07 mm; repeat difference 0.03±0.02 mm), which shows no bias in the system 600 using said device 100. Linear regression showed a nearly perfect linear relationship between the device 100 measurements and the true/known dimension (Accuracy: PVB=1.01*Known; $R^2$=0.98) and repeat device 100 measurements (Repeatability: PVB#1=1.0*PVB#2; $R^2$=1). Direct compliance measurements were made in vivo using a fluid filled pressure transducer, as shown in FIG. 10C. Similar to bench, vessel compliance responses (determined from $\Delta CSA/\Delta P$) were highly repeatable and in agreement with prior studies. The insulative environment of balloon 104 allows for these highly accurate and repeatable results to occur on the bench and in vivo.

As additional background, venous outflow obstruction can produce chronic venous insufficiency (CVI), a complex disease which leads to venous thrombosis, distal hypertension, reflux and venous remodeling. Clinical presentations of these abnormalities range from pain, edema, and skin changes to ulceration. The treatment of these symptoms requires 2% of total health-care budgets for Western societies. Despite the alarming prevalence and cost of outflow obstructions and CVI, the ability to manage this disease and improve patient outcomes remains limited.

Current management, prior to the disclosure of the present application, includes surgical procedures such as ligation, ablation, sclerotherapy, venoplasty and segment transplantation. More recent advances have shifted towards endovenous approaches, namely stenting. Unfortunately, these approaches are associated with poor long-term outcomes and remain largely ineffective in attenuating post-thrombotic syndrome. Although longer follow-ups indicate primary 5-10 year patency rates are 66% which is increased by concomitant venoplasty, the cumulative healing rate for venous ulcers is only 55%. Thus, non-surgical options remain palliative and endovenous stenting has limited success in these patients as supported by 25-29% of patients requiring one or more reinterventions. Moreover, stenting often fails to ameliorate reflux which in some cases is made worse. As such, nearly half of patients treated continue to experience claudication at five-year follow-ups, a finding strongly associated with ulceration, chronic venous reflux and stent failure. Due to the inability for stenting to attenuate post-thrombotic syndrome and the effect symptoms of CVI have on quality of life, there has been a growing need to refine endovenous revascularization in terms of lesion assessment and stent delivery.

Adaptation of technical approaches and guidelines used in arterial stenting does not apply to diseased venous segments, in part due to differences in the local mechanical (highly compliant) and biochemical (lower oxygen tension) environment. A major limitation continues to be diagnostic and delivery approaches which fail to take into account the venous compliance that contributes to 20-30% of stent recoil and hence, has a profound effect on stent diameter, foreshortening and therefore accurate stent deployment. This sets the stage for restenosis and potential migration as the lesion and recoil squeezes the stent away spontaneously or during post-dilatation[9]. Additional concerns for improper sizing and delivery is noted by the majority of iliofemoral stents protruding into the iliocaval confluence where "jailing" and subsequent ipsilateral stenting is often required to prevent adjacent outflow obstructions. Importantly, regions of compression at stent ends or confluence elongation have been associated with locations of restenosis and thrombosis which is directly related to inadequate stent expansion against lower compliant diseased venous segments. These findings are attributable to a poor understanding of lesion morphology, size and compliance of diseased venous segments that stem from inaccurate diagnostics and subsequent stent selection and delivery.

Prior to the disclosure of the present application, no accurate method existed for real-time quantitative venous lesion and reference vessel determination during venous stenting. Venographic assessment (with marked wires/catheters) and pressure surrogates during balloon expansion generally provide inaccurate cross-sectional estimates for balloon dimension, and thus, may require multiple post-dilatations and IVUS confirmations to achieve the desired stent diameter. Pressure/volume relationships have been used for sizing in peripheral balloon catheters, but said systems have limited accuracy because they provide sizing based on an average size across the entire balloon as opposed to a precise, profiled balloon sizing measurement as provided in detail herein when using an exemplary device 100 of the present disclosure. Despite the utility of IVUS, it is not used routinely in the clinic because of the added time, complexity, subjective interpretation of images, device cost, and required training associated with its usage. Angiography (both visual estimation/"eye balling" and quantitative angiography or "QA"), on the other hand, is used more routinely but lacks accuracy for sizing because of spatial resolution (i.e., two-dimensional slice projection of a three-dimensional vessel) and irregularity of vessel geometry (i.e., non-circular diseased vessels). Other studies have placed IVUS inside balloons which requires user interpretation (i.e., not real-time), and requires an increased catheter size to accommodate both the transducer and the balloon which is a practical limitation for low profile devices needed to cross venous occlusions. In view of the foregoing, the various device 100 and system 600 embodiments of the present disclosure solve the problems noted above and address the need to be able to accurately provide venoplasty balloon size, compliance and radial force during inflation to assess the degree of occlusion and compression for accurate stent selection and controlled stent delivery. Accordingly, various devices 100 and/or systems 600 of the present disclosure can be used in connection with treatments for various chronic venous diseases, including, but not limited to, CVI.

As noted herein, vein size can be determined accurately by injecting a small alternating electrical current within balloon 104 of device 100 during inflation and opposition against a venous valve wall. Conductance-based sizing measurements can be made in real-time during balloon 104 inflation, displayed on an easy-to-read bed-side console screen (such as a data acquisition and processing system 602 referenced herein), and provided as an objective CSA and diameter sizing assessment (as no manual measurements or interpretation required by the physician) independent of lesion symmetry. Devices 100 of the present disclosure are easy to use and only require a simple, sterile hook-up to a bed-side display console (wired or wirelessly, as applicable). Since there is no physician-required calibration of devices 100, use of an exemplary device 100 fits easily within the current workflow of the venous stenting procedure (i.e., no added time). The balloon 104 provides accurate sizing results with any type of saline/contrast mixtures used during inflation/deflation and can accurately size the full range of possible lesion sizes (e.g., ~2-18 mm) since the conductance measurements are made inside the insulative balloon 104, which allows for excellent accuracy in any environment. The balloon 104 contains multiple sets of measurement electrodes 120 that provide axial sizing profile along the length of the balloon 104. The venous lesion is the minimum diameter seen in the profile (since the balloon 104 will be opposed and smallest at the lesion). Multiple measurements along the length of the balloon 104 provides a benefit because it does not require the physician to precisely place the middle of the balloon 104 in the lesion at inflation, which is often difficult to achieve (i.e., minimum measurement anywhere in the profile will indicate the lesion size relative to the reference diameter by anatomical definition). The technology is highly versatile and can be used in other applications, including sizing for post-dilatation and stent delivery balloons, drug eluting balloons, cutting balloons, cryoplasty, as well as pulmonary venoplasty and mitral valve sizing. Thus, devices 100 and systems 600 of the present disclosure provide an innovative, clinically-seamless, real-time, simple, accurate, repeatable, and objective sizing measurement during venoplasty and pre-dilatation. Integration of compliance and radial force will provide assessment of lesion morphology that can aid in appropriate stent selection and delivery.

While various embodiments of devices and systems for determining vein geometric and compliance profiles for venous stenting and methods to use the same have been described in considerable detail herein, the embodiments are merely offered as non-limiting examples. It will therefore be understood that various changes and modifications may be made, and equivalents may be substituted for elements thereof, without departing from the scope of the present disclosure. The present disclosure is not intended to be exhaustive or limiting with respect to the content thereof.

Further, in describing representative embodiments, the present disclosure may have presented a method and/or a process as a particular sequence of steps. However, to the extent that the method or process does not rely on the particular order of steps set forth therein, the method or process should not be limited to the particular sequence of steps described, as other sequences of steps may be possible. Therefore, the particular order of the steps disclosed herein should not be construed as limitations of the present disclosure. In addition, disclosure directed to a method and/or process should not be limited to the performance of their steps in the order written. Such sequences may be varied and still remain within the scope of the present disclosure.

The invention claimed is:

1. A device, comprising:
   an elongated body configured to fit within a mammalian luminal organ;
   a balloon coupled to the elongated body, the balloon capable of and configured for inflation and deflation within the mammalian luminal organ;
   at least two excitation electrodes positioned along the elongated body within the balloon;
   a plurality of at least three detection electrodes positioned in between at least two of the at least two excitation electrodes; and
   a temperature sensor positioned within the balloon;
   wherein when the elongated body is at least partially inserted into the mammalian luminal organ, wherein when an unheated fluid is introduced into the balloon, and wherein when at least two of the at least two excitation electrodes generate an electric field, a first pair of two adjacent detection electrodes of the at least three detection electrodes can detect the electric field and obtain a first conductance measurement within the balloon, and a second pair of two adjacent detection electrodes of the at least three detection electrodes can detect the electric field and obtain a second conductance measurement within the balloon, the first conductance measurement and the second conductance measurement indicative of different locations within the balloon; and
   wherein the device is configured to obtain pressure data in addition to the first conductance measurement and the second conductance measurement, wherein dimensional data from the first conductance measurement or the second conductance measurement along with the pressure data provide compliance data at one or more locations within the mammalian luminal organ.

2. The device of claim 1, wherein the unheated fluid within the balloon is at room temperature.

3. The device of claim 1, wherein a plurality of conductance measurements in addition to the first conductance measurement and the second conductance measurement can be obtained within the balloon using at least two of the at least three detection electrodes.

4. The device of claim 3, wherein the plurality of conductance measurements are indicative of various stages of balloon inflation.

5. The device of claim 2, further comprising:
   at least one additional element in communication with an inner lumen of the balloon, the at least one additional element comprising a pressure sensor.

6. The device of claim 1, wherein the device is configured to obtain a plurality of conductance measurements, used to determine a plurality of cross-sectional areas, along a length of the balloon at various inflation pressures, the plurality of conductance measurements used to generate a profile of the balloon, corresponding to dimensions of the mammalian luminal organ.

7. The device of claim 1, further defining a suction/infusion port defined within the elongated body and in communication with a lumen defined within the elongated body.

8. The device of claim 1, forming at least part of an impedance system, the impedance system further comprising a data acquisition and processing system.

9. The device of claim 8, wherein the data acquisition and processing system is configured to display the first conductance measurement and the second conductance measurement in real time.

10. The device of claim 1, wherein the plurality of at least three detection electrodes comprises a plurality of at least seven detection electrodes forming six consecutive adjacent pairs of detection electrodes.

11. The device of claim 1, wherein the plurality of at least three detection electrodes comprises a plurality of at least seventeen detection electrodes forming sixteen consecutive adjacent pairs of detection electrodes.

12. A method, comprising the steps of:
    inserting at least part of a device into a mammalian luminal organ, the device comprising:
       an elongated body configured to fit within the mammalian luminal organ,
       a balloon coupled to the elongated body, the balloon capable of and configured for inflation and deflation within the mammalian luminal organ,
       at least two excitation electrodes positioned along the elongated body within the balloon,
       a plurality of at least three detection electrodes positioned in between at least two of the at least two excitation electrodes, and
       a temperature sensor within the balloon;
    inflating the balloon with an unheated fluid within the mammalian luminal organ so that the balloon contacts the mammalian luminal organ;
    obtaining a first conductance measurement within the balloon by exciting an electric field using the at least two excitation electrodes and detecting the electric field using a first pair of two adjacent detection electrodes; and
    obtaining a second conductance measurement within the balloon by detecting the electric field using a second pair of two adjacent detection electrodes different from the first pair of two adjacent detection electrodes, the first conductance measurement and the second conductance measurement indicative of different locations within the balloon.

13. The method of claim 12, further comprising the step of:
    generating a profile of the mammalian luminal organ based upon the first conductance measurement and the second conductance measurement.

14. The method of claim 13, further comprising the steps of:
    selecting an appropriately sized stent based upon the profile; and
    placing the appropriately-sized stent within the mammalian luminal organ.

15. The method of claim 13, wherein the profile indicates a lesion or other vascular abnormality within the mammalian luminal organ, and wherein the placing step is performed to place the appropriately-sized stent within the mammalian luminal organ at the lesion or other vascular abnormality.

16. The method of claim 14, wherein the mammalian luminal organ is a vein, and wherein the stent is ultimately placed within the vein.

17. The method of claim 12, wherein the method is performed to identify portions of/the mammalian luminal organ that are relatively more or less compliant than other portions of the mammalian luminal organ.

18. The method of claim 12, wherein at least one of the steps of obtaining a first conductance measurement and obtaining a second conductance measurement is performed in connection with obtaining at least one pressure measurement and/or at least one temperature measurement within the balloon.

19. A method of treating a luminal organ disease, comprising the steps of:
- inserting at least part of a device into a mammalian luminal organ, the device comprising:
  - an elongated body configured to fit within the mammalian luminal organ,
  - a balloon coupled to the elongated body, the balloon capable of and configured for inflation and deflation within the mammalian luminal organ,
  - at least two excitation electrodes positioned along the elongated body within the balloon,
  - a plurality of at least five detection electrodes positioned in between at least two of the at least two excitation electrodes, and
  - a temperature sensor within the balloon;
- inflating the balloon with an unheated fluid within the mammalian luminal organ at a lesion or other vascular abnormality so that the balloon contacts the mammalian luminal organ;
- obtaining at least four conductance measurements within the balloon by exciting an electric field using the at least two excitation electrodes and detecting the electric field using a first pair of two adjacent detection electrodes, a second pair of two adjacent detection electrodes, a third pair of two adjacent detection electrodes, and a fourth pair of two adjacent detection electrodes, each of the four conductance measurements indicative of different locations within the balloon;
- generating a profile of the mammalian luminal organ based upon the at least four conductance measurements, the profile identifying a location of the lesion or other vascular abnormality relative to the balloon and a size of the lesion relative to other portions of the mammalian luminal organ;
- identifying an appropriately-sized stent based upon the size of the lesion or other vascular abnormality; and
- placing the stent within the mammalian luminal organ at the location of the lesion or other vascular abnormality identified by the profile.

20. The method of claim 19, wherein the step of obtaining at least four conductance measurements is performed in connection with obtaining at least one pressure measurement and/or at least one temperature measurement of the unheated fluid within the balloon.

* * * * *